(12) United States Patent (10) Patent No.: US 9,089,289 B2
Gruppetta (45) Date of Patent: Jul. 28, 2015

(54) OPTICAL IMAGING SYSTEM

(75) Inventor: Stephen Gruppetta, London (GB)

(73) Assignee: CITY UNIVERSITY, London (GB)

( * ) Notice: Subject to any disclaimer, the term of this patent is extended or adjusted under 35 U.S.C. 154(b) by 45 days.

(21) Appl. No.: 13/882,596

(22) PCT Filed: Nov. 3, 2011

(86) PCT No.: PCT/EP2011/069375
§ 371 (c)(1),
(2), (4) Date: Aug. 5, 2013

(87) PCT Pub. No.: WO2012/059564
PCT Pub. Date: May 10, 2012

(65) Prior Publication Data
US 2013/0301002 A1 Nov. 14, 2013

(30) Foreign Application Priority Data
Nov. 3, 2010 (GB) .................................. 1018560.1

(51) Int. Cl.
*A61B 3/14* (2006.01)
*A61B 3/12* (2006.01)
*A61B 3/113* (2006.01)
*A61B 3/00* (2006.01)
(Continued)

(52) U.S. Cl.
CPC .................. *A61B 3/12* (2013.01); *A61B 3/0008* (2013.01); *A61B 3/102* (2013.01); *A61B 3/113* (2013.01); *A61B 3/13* (2013.01); *A61B 3/14* (2013.01)

(58) Field of Classification Search
CPC ............ A61B 3/14; A61B 3/12; A61B 3/102; A31B 3/14; A31B 3/12; A31B 3/145; A31B 3/102
USPC .................................................. 351/200–221
See application file for complete search history.

(56) References Cited

U.S. PATENT DOCUMENTS

| 5,528,369 A | 6/1996 | Starkey |
| 5,949,521 A * | 9/1999 | Williams et al. ............... 351/246 |
| 2002/0057438 A1 * | 5/2002 | Decker ......................... 356/601 |

(Continued)

FOREIGN PATENT DOCUMENTS

| EP | 1123689 | 8/2001 |
| EP | 1950526 | 7/2008 |

(Continued)

OTHER PUBLICATIONS

Shamir, Joseph. Optical Systems and Processes. 1999. SPIE—The International Society for Optical Engineering.pp. 163-168.*
Gruppetta, Steve et al., "Theoretical Study of Multispectral Structured Illumination for Depth Resolved Imaging of Non-Stationary Objects: Focus on Retinal Imaging", Biomedial Optics Express, vol. 2, No. 2, Jan. 5, 2011, pp. 255-263; XP55019205.
(Continued)

*Primary Examiner* — Ricky Mack
*Assistant Examiner* — Kristina Deherrera
(74) *Attorney, Agent, or Firm* — Jason H. Vick; Sheridan Ross, PC

(57) ABSTRACT

An optical imaging system (1) for in-vivo retinal imaging, the system (1) comprising: an optical source (3) for generating incoherent light in a plurality of wavelength bands; an optical imaging sub-system (6) configured to split light from said optical source (3) into a plurality of beams, to introduce a path difference between said beams of light, and recombine those beams to form interference fringes that are imaged on a subject (21); and an image capture device (29) configured to capture light from the subject (21) being imaged, and to form an image of said subject (21).

10 Claims, 3 Drawing Sheets

(51) Int. Cl.
*A61B 3/10* (2006.01)
*A61B 3/13* (2006.01)

(56) References Cited

U.S. PATENT DOCUMENTS

| | | | |
|---|---|---|---|
| 2004/0061865 A1 | 4/2004 | Drabarek | |
| 2004/0156016 A1* | 8/2004 | Kerr et al. | 351/206 |
| 2004/0239942 A1 | 12/2004 | Sun | |
| 2005/0185192 A1 | 8/2005 | Kim et al. | |
| 2009/0046164 A1 | 2/2009 | Shroff et al. | |

FOREIGN PATENT DOCUMENTS

| | | |
|---|---|---|
| GB | 2485274 | 5/2012 |
| JP | 2000-346612 | 12/2000 |
| WO | WO 96/24082 | 8/1996 |

OTHER PUBLICATIONS

International Search Report for corresponding International Application No. PCT/EP2011/069375, mailed Mar. 6, 2012.
Written Opinion for corresponding International Application No. PCT/EP2011/069375, mailed Mar. 6, 2012.
Search Report for corresponding Great Britain Application No. GB1018560.1.
Search Report for corresponding Great Britain Application No. GB1119015.4, mailed Feb. 9, 2012.
U.S. Appl. No. 14/694,153, filed Apr. 23, 2015, Gruppetta.
International Preliminary Report on Patentability for corresponding International Application No. PCT/EP2011/069375, mailed May 7, 2013.

* cited by examiner

OPTICAL IMAGING SYSTEM

CROSS REFERENCE TO RELATED APPLICATIONS

This application is a national stage application under 35 U.S.C. 371 of PCT Application No. PCT/EP2011/069375 having an international filing date of 3 Nov. 2011, which designated the United States, which PCT application claimed the benefit of Great Britain Application No. 1018560.1 filed 3 Nov. 2010, each of which are incorporated herein by reference in their entirety.

FIELD OF THE INVENTION

This invention relates to optical imaging systems, particularly to optical systems for in-vivo imaging. In one envisaged implementation, the invention is particularly useful for in-vivo imaging of the eye—in particular of the retina. In other envisaged implementations, the teachings of the invention may readily be applied to microscopy.

To facilitate a proper understanding of the teachings of the present invention, particular embodiments will be described below with particular reference to in-vivo imaging of the eye, in particular the retina, of a subject. It should be remembered, however, that this application is merely illustrative and is not intended to be a limitation of the scope of the present invention.

BACKGROUND TO THE INVENTION

A variety of different devices have previously been proposed for in-vivo imaging of a subject's eye. Such devices are typically used by a clinician or physician to look for abnormalities (congenital or acquired) and symptoms of disease.

One such previously proposed device is the so-called "ophthalmoscope". Commonly available opthalmoscopes range from relatively simple pocket-sized opthalmoscopes such as the Welch Allyn PocketScope™ Ophthalmoscope, to more complex devices such as the Welch Allyn Panoptic™ Ophthalmoscope (each of which are available from Welch Allyn Inc., Corporate Headquarters, 4341 State Street Road, Skaneateles Falls, N.Y. 13153-0220, USA and viewable at: www.welchallyn.com). In general terms, such devices allow an operator to shine a light into a subject's eye to illuminate the retina whilst the operator looks for abnormalities and symptoms of disease.

A more sophisticated device for imaging the retina of a subject is the so-called Scanning Laser Ophthalmoscope (often referred to as an "SLO"). The SLO is more accurate than a traditional ophthalmoscope and provides a greater field of view of the retina. The SLO comprises a laser source and a series of vertical and horizontal mirrors that can be operated to scan the laser over a subject's retina to generate a raster image that can be displayed on a conventional television monitor.

Whilst the SLO is able to image the retina in real time, reflections from the eye, astigmatism and higher order aberrations introduced by the cornea, tear film, lens and eye movements, can cause problems with the data produced by the device, resulting in poorer images. To address these issues, a device known as an Adaptive Optics Scanning Laser Ophthalmoscope (AOSLO) has more recently been proposed. This device uses adaptive optics to remove optical aberrations from images obtained with an SLO. In particular, in an AOSLO, a laser is collimated and then reflected off of a beam-splitting mirror. As with a conventional SLO, light is passed through both a horizontal and a vertical scanning mirror before and after the eye is scanned to align the moving beam for eventual retinal raster images of the retina. Additionally, the light is reflected off of a deformable mirror before and after exposure to the eye to compensate for optical aberrations. The laser enters the eye through the pupil to illuminate the region it has been focused onto and light reflected back passes to a beam splitter where it is directed simultaneously toward a photomultiplier tube (PMT) and toward a Shark-Hartmann wavefront sensor array. The light going toward the photomultiplier is focused through a confocal pinhole to remove light not reflecting off of the plane of interest and is then recorded in the PMT. Light directed to the wavefront sensor array is split up by the lenslets in the array and then recorded onto a Charge-coupled device (CCD) camera for detection of optical aberrations. These aberrations are optically compensated for by using the deformable mirror to increase lateral and axial resolution.

Another commonly used technique is called Optical Coherence Tomography (OCT). OCT provides a powerful clinical tool for monitoring retinal physiology in patients, and utilises low coherence interferometry to differentiate tissues within the eye and create a cross section of a living patients' retina non-invasively. OCT provides better axial resolution than AOSLO, however AOSLO represents tends to provide better translational resolution than OCT and can thus be used to track minor lateral physical changes, such as the effects of eye movements on the retina. A combination of AOSLO and OCT has also recently been proposed, which combination should provide, at high speed, three dimensional images of individual cone cells and an illustration of the overall cone mosaic near the fovea of a subject's eye.

Whilst these devices are all of use in imaging the eye of a subject, a principal problem with SLO, AOSLO and OCT devices is that they are relatively expensive, typically in the order of tens of thousands of pounds. The effect of this is that such devices tend not to be available to individual or small groups of practitioners, and instead tend to be limited to larger organisations, such as hospitals.

One technique that might be employed to address this issue is broadly similar to a technique that is commonly referred to as "structured illumination microscopy". Structured illumination microscopy enables optical sectioning of a three-dimensional (3D) object resulting in images similar to those obtained using a confocal scanning microscope. It has also been used for enhanced lateral resolution, allowing super-resolution beyond the diffraction limit. In the depth-resolving case, the basic principle between structured illumination microscopy and confocal microscopy is similar, namely that only planes that are in focus are imaged efficiently and out-of-focus planes contribute significantly less to the image.

However they are fundamentally different optical systems. Structured illumination microscopy has the advantage of being an optically simple technique that does not require laser illumination nor scanning of the beam or sample. The non-scanning configuration of the structured illumination microscope and the absence of a laser source enable a simple optical set up to be used that has minimal moving parts, and thus has potential for cost-effectiveness and robustness.

Another drawback of the confocal microscope is that the detector pinhole rejects light in order to achieve axial sectioning, and in practice, especially in the ophthalmic imaging case of the confocal Scanning Laser Ophthalmoscope (SLO), trade offs have to be made between pinhole size and confocality, thus limiting the axial sectioning capabilities of the device. Structured illumination microscopy does not reject any light and can therefore image the sample more efficiently.

In structured illumination microscopy, the sample is illuminated with a sinusoidal pattern along one of its lateral dimensions. For weak objects, it has been shown that it is only the zero-order spatial frequency that does not attenuate with defocus. As it is possible with sinusoidal illumination to recover an image in which the zero-order term is absent; all remaining spatial frequencies tend to attenuate with defocus thereby providing that the in-focus plane is the one that contributes most significantly to the image obtained. A drawback of this technique is that it is necessary to acquire three successive images with the sinusoidal pattern displaced by phases of $\frac{2}{3}\pi$ and $-\frac{2}{3}\pi$ with respect to the first image. From these three images, an optically sectioned image of the sample can be obtained.

Whilst this approach appears useful, in the context of imaging non-stationary objects the requirement for multiple images proves problematic. This is particularly the case in the context of in-vivo retinal imaging where involuntary and voluntary tremors and saccades of the eye result in a typically continuously moving sample.

Another problem to be addressed is the manner in which the retina, in this particular example is to be illuminated. In particular in one technique known as "grid projection", the frequency of the sinusoid needs to be carefully controlled so that the resultant frequency of the light illuminating the retina is in the region of 500 cycles per degree. However, a problem with this approach is that the optics of the eye does not transmit a sinusoid with a frequency above about 60 cycles per degree.

One way to address this last problem is to illuminate the retina with coherent sources that are allowed to interfere and thereby generate fringes on the retina. However, if coherent sources are used, all layers of the eye may an equal contribution and hence the ability to image the retina in three-dimensions is lost.

One previously proposed attempt to resolve these issues is disclosed in US2009/0046164. In this patent application the system disclosed is primarily intended to provide lateral superresolution (i.e. lateral resolution beyond the Rayleigh limit), and hence axial resolution (or in other words, three-dimensionality) is not of concern. This patent discloses the use of grid projection techniques using incoherent light, and fringe projection techniques using coherent laser light. However, incoherent grid projection techniques cannot function as a means to image the retina in-vivo due to the aforementioned transmission limit of around 60 cycles per degree (it would, of course, function adequately when used to image a sample in-vitro), and fringe projection techniques using coherent laser sources cannot provide axial resolution. In addition, in this patent application the aforementioned problem with a subject moving between successive images is countered by two different techniques, in one technique where the movement concerned is anticipated, phase shifts are estimated a priori. In another technique where movements cannot be anticipated, an algorithm is employed to estimate phase shifts a posteriori from peaks in the Fourier transform. As will be appreciated, in either case the accuracy of the resulting image is only as good as the phase shift estimations.

The present invention has been devised with the foregoing problems in mind.

SUMMARY OF THE INVENTION

In accordance with a presently preferred embodiment of the present invention, there is provided an optical imaging system for in-vivo retinal imaging, the system comprising: an optical source for generating incoherent light in a plurality of wavelength bands; an optical imaging sub-system configured to split light from said optical source into a plurality of beams, to introduce a path difference between said beams of light, and recombine those beams to form interference fringes that are imaged on a subject; and an image capture device configured to capture light from the subject being imaged, and to form an image of said subject.

In another aspect, the invention provides an imaging method for in-vivo retinal imaging, the method comprising: operating an optical source to generate incoherent light in a plurality of wavelength bands; splitting light from said optical source into a plurality of beams, introducing a path difference between said beams of light, and recombining those beams to form interference fringes that are imaged on a subject; capturing light from the subject being imaged, and forming an image of said subject.

Other aspects and features of the invention are set out in the dependent claims, and further features and advantages of aspects of the invention are set out hereafter.

BRIEF DESCRIPTION OF THE DRAWINGS

Various aspects of the teachings of the present invention, and arrangements embodying those teachings, will hereafter be described by way of illustrative example with reference to the accompanying drawings, in which.

DETAILED DESCRIPTION OF PREFERRED EMBODIMENTS

Figure 1:
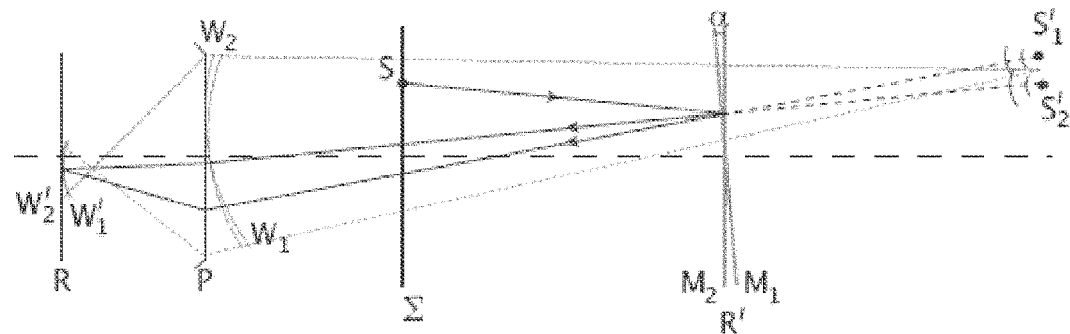
FIG. 1 is a schematic representation of an optical imaging system with all branches of an interferometer superimposed for clarity.

Before embarking on a detailed description of preferred embodiments, it is appropriate at this juncture to provide a general explanation of the scientific theory on which aspects and teachings of the present invention rely. Specific reference will be made below to in-vivo retinal imaging, but it should be remembered (as mentioned previously) that this particular application of the teachings of the present invention is merely illustrative and not intended to be a limitation of the scope of the present invention.

In very general terms, the teachings of the present invention concern a novel implementation of structured illumination in which three images with displaced sinusoidal illumination are acquired simultaneously instead of sequentially, thus avoiding the aforementioned difficulties associated with imaging by non-stationary subjects, such as in-vivo imaging of a subject's retina.

In one envisaged implementation this is achieved by illuminating a subject to be imaged, such as the retina, with three different wavelengths each projecting a sinusoidal pattern with the required phase. In a particularly preferred implementation the wavelengths are chosen to match the peak responsivity of the three detector types in a standard colour CCD camera so that, after appropriate filtering to reduce cross-talk, the three required images can be extracted from the three colour channels of a single image from the CCD camera from which the final optically sectioned image can be retrieved.

The resulting multispectral image will be a result of three sub-images that are not exactly identical owing to the difference in reflectivity of the imaged layer for each of the three wavelengths. However, the spatial frequency of the grid will be high with respect to the structures being imaged (as discussed below) and therefore any artefacts will be small. Furthermore, in practical situations it is likely that a number of successive optically sectioned images will be aligned and averaged to improve contrast and reduce noise, and in this scenario the non-stationarity of the object is now advantageous as the averaging process is likely to cause any inhomogeneities due to wavelength differences in a given single image also to be averaged. The final image will therefore be a composite of three wavelengths, likely to yield more information than a monochromatic image.

As mentioned briefly above, when imaging the human retina, standard structured illumination microscopy encounters a further problem that makes its application to retinal imaging problematic. Conventionally, the structured pattern illuminating the sample is achieved in one of two ways, namely grid projection or fringe projection.

In the former, a sinusoidal grid is illuminated incoherently and imaged onto the sample, in the latter a laser beam is used to generate a coherent fringe pattern on the sample. However, it has been shown that axial sectioning can only be obtained under incoherent imaging and therefore the fringe projection method can only be used for fluorescence microscopy as the incoherence is obtained through the mutual independence of the fluorofores. Since non-invasive retinal imaging is not a fluorescence technique, fringe projection cannot be used.

In addition, grid projection is limited by the Modulation Transfer Function (MTF) of the condenser lens as the spatial frequency of the grid affects the axial resolution. Because of the relatively poor optics of the human eye (which acts as both condenser and objective in retinal imaging) the highest spatial frequency that can be obtained by the grid projection technique (typically about 60 cycles per degree (cpd), this being the frequency cut-off of a typical eye) is too low for achieving the desired axial resolution.

The technique embodied by the teachings of the present application addresses these issues by adopting a novel fringe projection technique. The technique, described in detail below, can project fringes whose spatial frequency is not limited by the optics of the eye (or more generally by the collector lens) and can illuminate the sample incoherently as is preferred for non-fluorescent axial sectioning using structured illumination.

In one envisaged implementation of the teachings of the invention, the aforementioned novel projection technique employs a Michelson interferometer in which an incoherent extended light source is used to project straight Fizeau fringes directly onto the retina (note however that this application is merely illustrative of the teachings of the invention, and that the teachings of the invention may more widely be applied—for example to structured illumination microscopy in general).

FIG. 1 is a schematic representation of a Michelson interferometer in which all branches are superimposed onto the same optical axis. The plane $\Sigma$ represents the extended incoherent light source, $M_1$ and $M_2$ represent the mirrors (one of which is actually the image of the mirror on a beamsplitter, not shown). The axial optical path length of the mirrors from the source is equal, though one mirror is tilted with respect to the other by a small angle $\alpha$. If we consider a point source S on the extended source $\Sigma$, then each mirror creates an image of this source, $S_1'$ and $S_2'$ respectively. The fringes are localised at the plane of the air wedge produced by the two mirrors, and therefore the eye will focus at the plane containing $M_1$ and $M_2$.

It is thus appropriate to consider that the light reaching the eye is coming from the two point sources $S_1'$ and $S_2'$ both of which are emitting diverging spherical waves, so that at the pupil plane P of the eye we can define wavefronts $W_1$ and $W_2$ coming from the respective sources. These wavefronts have the same curvature since the two sources $S_1'$ and $S_2'$ are equidistant from the eye for small angle $\alpha$, and their respective tilt is $\alpha$. As the eye is focused at the plane containing the $M_1$ and $M_2$, these wavefronts will focus before the retina R (as shown by the dotted red lines in FIG. 1) and we can therefore define two diverging wavefronts $W_1'$ and $W_2'$ at the retina that are again substantially identical except for tilt. The interference produced by these wavefronts forms an interference pattern on the retina that consists of a plurality of parallel straight fringes. It should be noted that because $\alpha$ is small, the angular subtense of the sources $S_1'$ and $S_2'$ at the eye can be assumed to be well within the isoplanatic patch of the eye, and as such any aberrations introduced at the pupil plane P of the eye will be common to both $W_1$ and $W_2$, and hence $W_1'$ and $W_2'$. Thus the fringe pattern produced is not affected by the optics of the eye and the spatial frequency of the sinusoidal pattern is only a function of the angle $\alpha$ and the wavelength $\lambda$. This holds for all point sources S on the extended incoherent source plane $\Sigma$, thereby providing an incoherently illuminated sinusoidal grid pattern whose spatial frequency can be tuned by rotating one of the mirrors to vary the angle $\alpha$. The phase of the illuminating sinusoidal pattern can be altered by moving one of the mirrors axially to alter the relative optical path difference between the two branches.

Since the Fizeau fringes produces are localised at the plane R' of the optical air wedge formed by the two mirrors, and hence at the retinal plane R conjugate to this plane, it is also necessary to consider the nature of the illumination for out-of-focus planes. At the localisation plane on the retina R, the interference pattern produced by the virtual point sources $S_1'$ and $S_2'$ due to the actual point source S of the extended source $\Sigma$ is only a function of the tilt $\alpha$. In other words, the interference at any point on the localisation plane depends only on the thickness of the air wedge at that point, as expected for Fizeau fringes (fringes of equal thickness). For out-of-focus planes this is no longer the case; the interference pattern produced by each point source S on $\Sigma$ is now also dependant on the location of the point source so that each point source will produce a pattern that has a slight phase shift with respect to its neighbour. As a result the pattern will now be dependant on the effective size of the extended source and the distance of the source from the mirrors. The aperture of any detection system (such as the eye) will also impact on the effective size of the source. Therefore in general, the modulation of the fringes will decrease with increasing defocus but the rate of change of the modulation with defocus depends on the system set up.

In an envisaged implementation where non-stationary objects are to be imaged, for example as occurs in in-vivo retinal imaging, an implementation of the teachings of the invention provides a Structured Illumination Ophthalmoscope, depicted schematically in FIG. 3 and described later in detail, that employs the simultaneous projection of fringes at three different wavelengths. In the particular implementation depicted in FIG. 3, each wavelength has an associated mirror and the spatial frequency and phase of each fringe pattern can be adjusted separately to give sinusoidal patterns with the same spatial frequency and relative phases of $\phi_0$, $\phi_0+2\pi/3$ and $\phi_0-2\pi/3$. As will be appreciated, the angle $\alpha$ affects the spatial frequency of the fringes at the plane of the mirrors $M_1$ and $M_2$ (FIG. 1). In practical cases, there will be a magnification which is less than unity between this plane and the retinal plane R. This magnification is a parameter that can be used to optimise the rate of change of spatial frequency of the illumination pattern with changing angle $\alpha$.

The image formation theory of the structured illumination microscope is well documented for grid projection and fringe projection techniques, and a similar approach can be adopted to formalise the theory for the novel fringe projection technique described herein.

Figure 2:
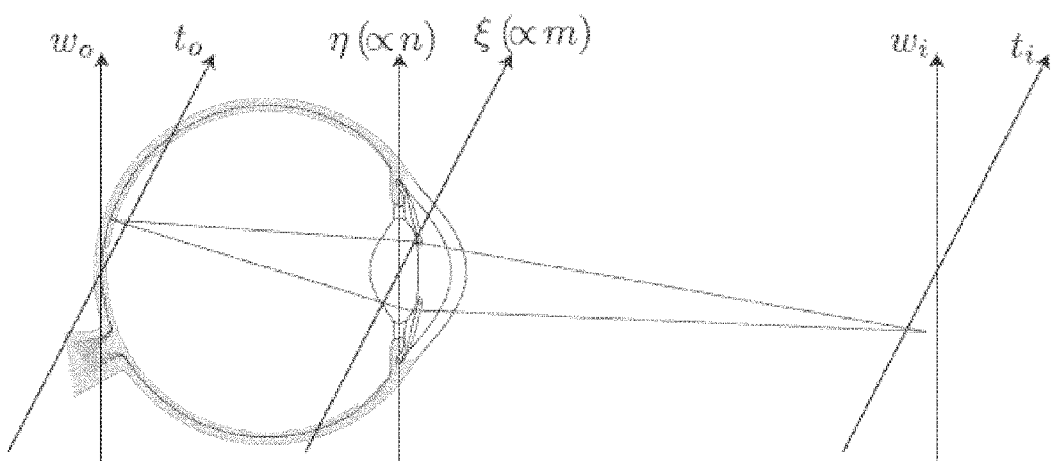
FIG. 2 is a diagrammatic representation of the geometry for an illustrative optical imaging system.

If we let $(x_O, y_O)$ represent the lateral coordinates at the object plane (i.e. in this specific example, the retina), we can then define the normalised coordinates $(t_o, w_o) = k(x_0, y_0) n \sin \alpha$ where $k=2\pi/\lambda$ and $n \sin a$ is the numerical aperture NA (FIG. 2 shows, for illustration, a simplified schematic of the imaging system). If the amplitude reflectance of the retina is $r(t_o, w_o)$ and it is illuminated by a structured incoherent intensity pattern given by:

$$I_{illumination}(t_o, w_o) + 1 + \mu \cos(vt_o + \phi), \quad (1)$$

where $\mu$ and $v$ are the modulation and frequency respectively of the sinusoidal pattern, and $\phi$ is the phase, then the object intensity becomes $$I_{object}(t_o, w_o) = [1 + \mu \cos(vt_o + \phi)] \rho(t_o, w_o), \quad (2)$$

where $\rho = |r|^2$ is the intensity reflectance of the retina. The intensity image of this object formed incoherently at the image plane $(t_i, w_i)$ is therefore $$I(t_i, w_i) = \iint [1 + \mu \cos(vt_o + \phi)] \rho(t_o, w_o) |h(t_i + t_o, w_i + w_o)|^2 dt_o dw_o, \quad (3)$$

where h is the amplitude point spread function of the objective (i.e. the optics of the eye). We assume unit magnification between object and image plane throughout these derivations, and integration is over all space. We can now expand this last equation using the expansion of cosine in terms of Euler's formula, and for compactness we pre-define the following functions:

$$I_0(t_i, w_i) = \iint \rho(t_o, w_o) |h(t_i + t_o, w_i + w_o)|^2 dt_o dw_o, \quad (4)$$

$$I_v(t_i, w_i) = \iint e^{ivt_o} \rho(t_o, w_o) |h(t_i + t_o, w_i + w_o)|^2 dt_o dw_o, \quad (5)$$

$$I_{-v}(t_i, w_i) = \iint e^{-ivt_o} \rho(t_o, w_o) |h(t_i + t_o, w_i + w_o)|^2 dt_o dw_o, \quad (6)$$

which yields $$I(t_i, w_i) = I_0(t_i, w_i) + \frac{\mu}{2} e^{i\phi} I_v(t_i, w_i) + \frac{\mu}{2} e^{-i\phi} I_{-v}(t_i, w_i). \quad (7)$$

$I_0(t_i, w_i)$ is simply the conventional incoherent image in a standard microscope with homogenous illumination ($\mu=0$), and we also note that $I_{-v} = I^*_v$ where * denotes the complex conjugate. The intensity image obtained using the structured illumination therefore can be considered as having three components, one of which is equivalent to the standard microscope. The relative weighting of these three components depends on the modulation of the illuminating pattern, $\mu$. Before proceeding to show that $I_v$ and $I_{-v}$ possess axial sectioning properties, we note that in order to extract these components we require more than one intensity image so that $I_0$ can be eliminated. Thus, three intensity images $I_1$, $I_2$ and $I_3$ are obtained with phases $$\varphi_1 = \varphi_0, \varphi_2 = \varphi_0 + \frac{2\pi}{3} \text{ and } \varphi_3 = \varphi_0 - \frac{2\pi}{3}$$

respectively. We can therefore show that the desired component can be obtained through either of the following two expressions:

$$|I_{\pm v}| = |I_1 + I_2 e^{\mp i2\pi/3} + I_3 e^{\pm i2\pi/3}|, \quad (8)$$

$$|I_{\pm v}| = \left(\frac{(I_1 - I_2)^2 + (I_1 - I_3)^2 + (I_2 - I_3)^2}{2}\right)^{\frac{1}{2}} \quad (9)$$

The conventional incoherent image can also be easily recovered from the three acquired images through;

$$I_0 = \frac{1}{3}(I_1 + I_2 + I_3) \quad (10)$$

We can now define the object intensity spectrum $\mathcal{R}(m,n) = \mathcal{F}\{\rho(t_0, w_0)\}$ where $\mathcal{F}$ represents the Fourier transform operator and $(m,n)$ are spatial frequencies corresponding to $(t_O, w_O)$, we can therefore substitute for $\rho$ in Eq. 5 to give $$I_v(t_i, w_i) = \iiiint e^{ivt_o} \mathcal{R}(m,n) e^{-i(nt_o + nw_o)} |h(t_i + t_o, w_i + w_o)|^2 dt_o dw_o dm dn. \quad (11)$$

Since, $P(m,n) = \mathcal{F}^{-1}\{h(t_o, w_o)\}$ where P is the generalised pupil function then through use of the shift theorem and autocorrelation theorem for Fourier transforms we have $$e^{i(mt_i + nw_i)} P(m,n) \otimes P^+(m,n) = \mathcal{F}^{-1}\{|h(t_o + t_i, w_o + w_i)|^2\} \quad (12)$$

$$= \int \int |h(t_o + t_i, w_o + w_i)|^2 e^{-i(mt_o + mw_o)} dt_o dw_o. \quad (13)$$

In anticipation of our final result we define the transfer function, and following a further application of the shift theorem to take into account the exponential term in Eq. 11 we get:

$$I_v(t_i, w_i) = e^{ivt_i} \iint \mathcal{R}(m,n) C(m+v, n) e^{i(nt_i + nw_i)} dm dn \quad (14)$$

In order to investigate the effect of defocus on the structured illumination microscope, we need to consider the effect of defocus on the illumination pattern. This is fairly straightforward for the grid projection and fringe projection techniques. In the former, as the illumination pattern is an image of a sinusoidal grid formed on the sample, the axial behaviour of the structured pattern is determined by the three-dimensional point spread function of the collector lens which is responsible for the illumination. The modulation of the sinusoidal pattern therefore decreases with defocus. In fringe illumination the sinusoidal pattern is formed through the interference of two laser beams and is independent of axial position; the modulation therefore does not decrease with defocus. For the novel fringe projection technique described herein, the defocus considerations are more involved as described above.

One practical scenario is the case when the extended source is small or distant so that we can assume all rays are nearly parallel to the optical axis. This is a valid assumption for an ophthalmic imaging system owing to the restrictions imposed by the pupil of the eye. In this case we can assume that the modulation μ of the sinusoidal pattern is not a function of defocus. Equation 3 can therefore be rewritten as $$I(t_i, w_i; u) = \iint [1 + \mu \cos(v t_o + \phi)] \rho(t_o, w_o; u) |h(t_i + t_o, w_i + w_o; u)|^2 dt_o dw_o, \quad (15)$$

where u is the normalised axial coordinate representing defocus, related to the actual axial coordinate z through $u = 4knz \sin\sin^2\alpha/2$. Similarly, all subsequent equations derived from Eq.3 become functions of u.

Therefore we note that the transfer function $C(m+v, n; u)$ of the structured illumination brightfield microscope with the (incoherent) fringe projection technique described herein is identical to the transfer function of a structured illumination fluorescence microscope illuminated with the (coherent) fringe projection technique, and will therefore express the same axial sectioning characteristics which are comparable to those of the confocal microscope. Similarly, the imaging system will exhibit an increase in lateral resolution owing to the higher cut-off frequency of $C(m+v, n; u)$ with respect to that of the standard incoherent microscope and the confocal microscope, for all non-zero values of v. It should be noted that the assumption leading to constant modulation of the structured pattern with defocus represents a worst case scenario, since any attenuation would lead to better axial sectioning. The choice of size and distance of the extended source in designing the system can therefore to some extent enhance the optical sectioning properties of the imaging system. On the other hand, the use of different wavelengths to obtain the three required intensity images, while making the technique feasible for ophthalmic use, will affect the axial sectioning capabilities as the $I_0$ term will not be fully eliminated in Eqs.8 and 9.

In the preceding paragraphs we have described and theoretically assessed a novel structured illumination technique that is well suited for the imaging of non-stationary objects, including in-vivo retinal imaging. The technique described includes a new technique for providing the sinusoidal illumination pattern that is required for structured illumination, namely a novel (incoherent) fringe projection technique, and a multiple wavelength illumination system that enables the three images required with phase-shifted structured patterns to be acquired simultaneously, rather than sequentially, thereby enabling moving objects to be imaged.

We have also shown that for practical implementations in the ophthalmic case, the theoretical axial sectioning is on a par with that obtained through fluorescence imaging through structured illumination with the coherent fringe projection system, and in the general case the geometry of the extended source in relation to the objective can be altered to further improve the achievable axial sectioning.

Figure 3:
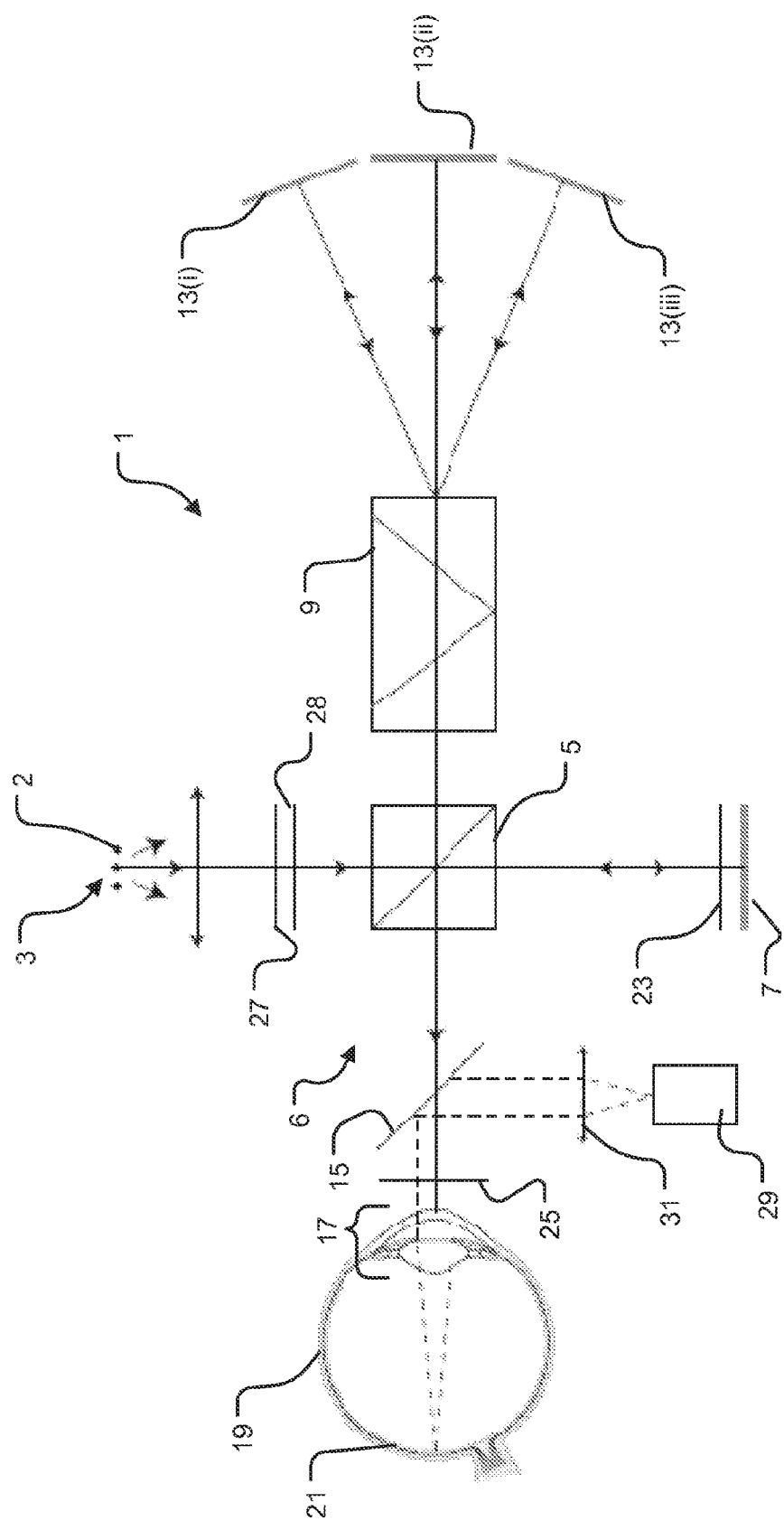
FIG. 3 is a diagrammatic representation of an optical imaging system according to an embodiment of the present invention.

Referring now to FIG. 3 of the accompanying drawings, there is depicted an optical system, hereafter referred to as a structured illumination ophthalmoscope (SIO) that embodies the teachings of the present invention.

The SIO 1 comprises an optical source 3 that is operable to generate incoherent light in three discrete wavelength bands. In one envisaged implementation the optical source comprises three light sources that are operable to generate incoherent light in respective discrete wavelength bands. In a preferred implementation one said light source comprises a source of red light, one a source of green light, and the last a source of blue light. In theory any incoherent source of light may be used, but in a particularly preferred arrangement each said light source comprises one or more light emitting diodes. In one envisaged arrangement depicted schematically in FIG. 4, the light source 3 comprises a plurality of red, green and blue light sources 2 (for example LEDs) arranged on a support 4, such as a PCB, so that when viewed from a distance the support appears to emit white light. In a particularly preferred arrangement the light sources 3 of each wavelength may be dispersed throughout the support 4 so that light of a given wavelength range is emitted from disparate point sources on the support.

Figure 4:
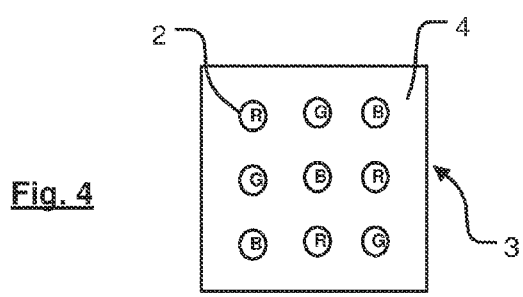
FIG. 4 is a schematic representation of an illustrative optical source.

In another envisaged implementation, which may be provided in combination with the arrangement shown in FIG. 4 or in combination with another arrangement of light sources, a rotating diffuser 28 may be provided so that the sources provide diffuse illumination. In another envisaged arrangement, a spatially incoherent source of illumination may be provided in place of a light source and diffuser. In either case, a polariser 27 may also be provided.

The light source 3 is configured to illuminate an optical sub-system 6 that comprises a Michelson interferometer. The interferometer comprises a first beamsplitter 5 which passes, in a manner known in the art, some of the incident light to a common reference mirror 7 in one branch of the interferometer, and reflects the remainder to a prism 9 in the other branch of the interferometer.

The prism 9 functions to split incident light from the beam splitter into discrete red, blue and green light beams that are each directed to an associated (preferably wavelength specific) mirror 13(i), (ii) and (iii). Optionally, to avoid cross-talk between different light sources, appropriate bandpass filters (not shown) may be inserted between the prism 9 and one or more of the mirrors 13.

Light reflected by the mirrors 13 travels back through the prism 9, and then through a second beamsplitter 15 before being focused by the optics 17 (including the pupil, lens and cornea) of the subject's eye 19 onto the retina 21. A half-wave plate 23 is provided between the first beamsplitter 5 and the common reference mirror 7 to control fringe modulation, and light returning through the half-wave plate is reflected by the first beamsplitter 5 through the second beamsplitter 15 and into the subject's eye 19. In a preferred implementation the second beamsplitter 15 is a polarising beamsplitter, and this polarising beamsplitter operates in conjunction with a quarter-wave plate 25 between the subject's eye and the second beamsplitter 15 to counteract reductions in returning light due to birefringence caused by the eye.

The common reference mirror 7 is moveable back and forth towards and away from the first beamsplitter 5, and the mirrors 13(i), (ii) and (iii) are moveable in two dimensions (towards/away and angularly) with respect to the prism 9. Movement of the mirrors 7, 13 adjusts the relative path lengths in each branch of the interferometer as well as adjusting the focus of the beams on the retina of the subject.

As will be appreciated by persons skilled in the art, the aforementioned Michelson interferometer may more generally be described as a means for splitting incident light into a number of beams, and introducing a path difference between those beams of light (that in this instance are each comprised of three colours, namely red, green and blue), and then recombining those beams to form interference fringes that are imaged on—in this instance—the retina of the subject.

Light reflected from the retina of the subject returns through the optics of the eye 17 and quarter-wave plate 25 before being reflected by the second beamsplitter 15 towards an image capture device 29, which may comprise an RGB CCD camera. In an envisaged implementation the RGB light sources are chosen to emit light in wavelength ranges that complement those that can be detected by the image capture device, and in a particularly preferred implementation the image capture device is configured to be capable of outputting R, G or B channels separately, or outputting a pseudo-colour image by combining respective channels. An imaging lens 31 (the like of which is known in the art) may be provided, if desired, to focus incident light onto the image capture device 29.

One advantage of this arrangement is that as certain structures within the eye are more responsive to light of particular wavelengths (for example, green light is particularly good for imaging blood vessels within the eye as haemoglobin in the blood absorbs red light and hence blood vessels tend to appear as dark regions on a brighter background) these structures can be imaged particularly well. Another advantage is that a pseudo-colour image inherently provides more information to the operator than would be discernable from a black/white or greyscale image.

In an alternative implementation, the single RGB image capture device could be replaced with discrete red, green and blue image capture devices and a prism or a series of frequency-specific beamsplitters/mirrors that divert respective colours to the associated imaging device. However such an arrangement would needlessly complicate the device without providing any discernable advantages, and hence is less preferred.

In the arrangement described above with reference to FIG. 3 of the drawings, three images of a subject's retina are simultaneously acquired and subsequently used to generate a three-dimensional image of the retina. By acquiring the images simultaneously, problems associated with movement of the subject's eye between images can be avoided.

In another application of the principles of the present invention, a SIO system is provided that captures successive images of the eye of a subject, and then generates a three-dimensional representation of the subject's retina from at least some of those images. In such a system, movement of the eye between successive images is quantified by illuminating the eye with a reference beam as each image is acquired, and then calculating the degree of eye movement that has occurred between successively captured images. Since movement of the eye causes a phase shift in the illuminating pattern from which the images are acquired, a determination of the degree of movement enables the phase shift in the illuminating pattern between successive images to be calculated, and by selecting three images attributable to light having relative phases of $\phi_0$, $\phi_0+2\pi/3$ and $\phi_0-2\pi/3$, or more than three images with other combinations of relative phase shifts, the images can be combined to provide a three-dimensional image of the subject's retina.

Figure 5:
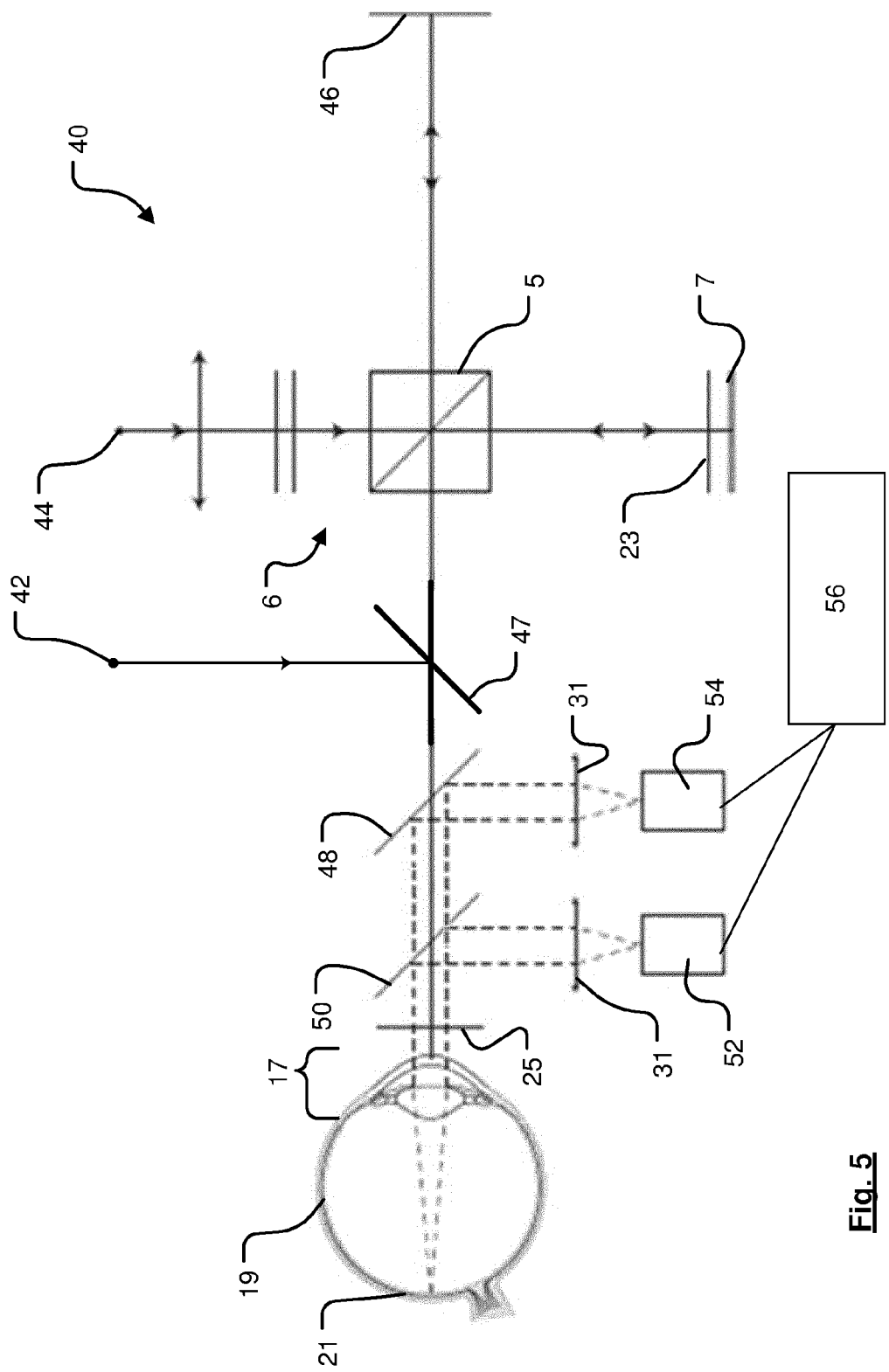
FIG. 5 is a diagrammatic representation of an optical imaging system according to an embodiment of the present invention.

FIG. 5 is a schematic representation of such a system 40 in which features common to the system depicted in FIG. 3 are labelled with the same reference numeral.

The system 40 includes a first optical source 42 that is configured to generate incoherent light at a reference wavelength (typically at a wavelength, such as infra-red (for example, 800 to 900 nm), that is not visible), and a second optical source 44 that is configured to generate incoherent light at a second wavelength different from that of the light from the first source 42.

The light source 44 is configured to illuminate an optical sub-system 6 that comprises a Michelson interferometer. The interferometer comprises a first beamsplitter 5 which passes, in a manner known in the art, some of the incident light to a common reference mirror 7 in one branch of the interferometer, and reflects the remainder to a mirror 46 in the other branch of the interferometer.

Light reflected by the mirror 46 travels back through the beamsplitter 5, and then through a second, a third and a fourth beamsplitter 47, 48 and 50 before being focused by the optics 17 (including the pupil, lens and cornea) of the subject's eye 19 onto the retina 21. A half-wave plate 23 is provided between the first beamsplitter 5 and the common reference mirror 7 to control fringe modulation, and light returning through the half-wave plate 23 is reflected by the first beamsplitter 5 through the second, third and fourth beamsplitters 47, 48 and 50 and into the subject's eye 19. In a preferred implementation at least one of the third and fourth beamsplitters 48, 50 is a polarising beamsplitter that operates in conjunction with a quarter-wave plate 25 between the subject's eye and the fourth beamsplitter 50 to counteract reductions in returning light due to birefringence caused by the eye.

The common reference mirror 7 is moveable back and forth towards and away from the first beamsplitter 5, and the mirror 46 is moveable in one dimension (towards/away) with respect to the beamsplitter 5. Movement of the mirrors 7, 46 adjusts the relative path lengths in each branch of the interferometer as well as adjusting the focus of the beams on the retina of the subject.

As will be appreciated by persons skilled in the art, the aforementioned Michelson interferometer may more generally be described as a means for splitting incident light into a number of beams, and introducing a path difference between those beams of light, and then recombining those beams to form interference fringes that are imaged on—in this instance—the retina of the subject.

Light from the light source 42 illuminates the aforementioned second beamsplitter 47 and is reflected through the third and fourth beamsplitters 48, 50 and quarter-wave plate 25 before being focussed by the optics 17 of the subject's eye 19 onto the retina 21.

The third and fourth beamsplitters 48, 50 are each configured to reflect light of a particular range of wavelengths. In one envisaged implementation, the fourth beamsplitter 50 is configured to reflect light from the first optical source 42, and the third beamsplitter 48 is configured to reflect light from the second optical source 44. By virtue of this arrangement, light reflected from the retina of the subject returns through the optics of the eye 17 and quarter-wave plate 25 before being reflected by one of the third and fourth beamsplitters 48, 50 towards an associated image capture device 52, 54, such as a video camera. Imaging lenses 31 (the like of which is known in the art) may be provided, if desired, to focus incident light onto the respective image capture devices 52, 54.

In a particularly preferred implementation, the camera 52 associated with the fourth beamsplitter 50 is tuned for detecting light of the wavelength emitted by the first source 42. The camera 54 associated with the third beamsplitter 48 may be tuned to detect light of the wavelength emitted by the second source 44, or in another envisaged arrangement the camera 54 associated with the third beamsplitter 48 may be configured to be sensitive to a broader range of wavelengths.

This latter arrangement is particularly useful, as it would allow the SIO depicted in FIG. 5 to be used for hyper- or multispectral imaging of a subject's retina. In such an implementation, by sweeping the wavelength at which light is emitted by the second source 44 over a wide range of wavelengths (and capturing images at each said wavelength) it would be possible to generate a hyper- or multispectral image of the retina, which image would allow certain structures within the eye (such as blood vessels) to be imaged particularly well. In a similar way, the arrangement shown in FIG. 3 may be used for hyper- or multispectral imaging by varying the wavelengths at which the light sources 3 emit light. Such wavelength variations may be introduced in a number of ways, for example by means of suitable filters.

Referring again to FIG. 5, the system 40 further comprises a processor 56, such as a computer, that is configured to process images from the respective cameras 52, 54. In particular, the processor is configured to use conventional digital image processing techniques (such as those described in Digital Image Processing ($2^{nd}$ Edition), by Gonzalez and Woods, published by Prentice Hall) to identify landmarks in an image and then track those landmarks as they move between successive frames of the signal from the camera 52. By tracking these landmarks the processor is able to determine a measure of the extent to which the eye being imaged has moved between successive images. The processor derives, from this measurement, an indication of the phase shift induced by the respective eye movements and selects three corresponding frames from the signal output by camera 54 that exhibit the required relative phase difference of $\phi_0$, $\phi_0+2\pi/3$ and $\phi_0-2\pi/3$, or selects more than three corresponding frames with other combinations of phase differences. The processor may then combine these images to generate a three-dimensional representation of the subject's retina.

In the foregoing it has been explained how the novel technique described herein can provide structured illumination imaging, particularly (but not exclusively) in the field of retinal imaging. The achievement of good lateral and axial resolution when imaging the living human retina is important for early detection and diagnosis of retinal disease, when treatment tends to be both more effective and more cost-efficient. Imaging devices that can resolve small retinal structures both laterally and in depth also aid clinicians who study these diseases, treatment and management.

The SLO was the first device to offer optical sectioning of the retina, and Optical Coherence Tomography (OCT) has the capability of achieving good axial resolution, but despite this the Structured Illumination Ophthalmoscope (SIO) described herein provides a number of advantages over existing systems.

For example, unlike the SLO and OCT techniques, the SIO does not employ lateral scanning as the illumination is wide-field. This makes the SIO a relatively simple device, at least optically, that does not rely on mechanical scanning devices and hence incur the optical design trade-offs associated with scanning systems. In addition to the potential for reduced design, engineering and production costs as compared with existing devices, the SIO avoids distortion due to intra-frame eye movements and other potential artefacts introduced by the scanning processes characteristic of SLO and OCT devices.

Another advantage is that the use of incoherent light sources in the SIO reduces speckle effects that can introduce artefacts particularly when imaging at higher resolutions. Another advantage is associated with the fact that as less of the illumination light is discarded at the sample, as compared with the confocal pinhole in the SLO or the interference conditions required in OCT, the SIO is light efficient. In the SLO in particular, the trade-off between having a small confocal pinhole size to provide higher axial resolution, and having sufficient signal-to-noise ratio at the detector is a major drawback that is mitigated by the SIO. This latter point is especially important in retinal imaging since the incident light on the sample is limited by ocular safety considerations. Yet another advantage is that the multispectral imaging characteristics of the SIO enables efficient imaging of more retinal layers and structures within a single image than previous techniques.

It is apparent, therefore, that in retinal imaging applications, the SIO provides axially sectioned images that are at least comparable to those of the SLO. It also offers a number of advantages over the SLO which include better light efficiency, improved lateral resolution, multi-spectral imaging and a marked reduction in optical and opto-mechanical complexity as no lateral scanning mechanisms are required. The latter point has implications in image quality but also in potential future development and manufacture costs, and maintenance and reliability of commercial devices. The potential for an inexpensive retinal imaging system with high quality 3D imaging capabilities is one of importance clinically in the drive to detect retinal disease early through screening.

It will be appreciated that whilst various aspects and embodiments of the present invention have heretofore been described, the scope of the present invention is not limited to the particular arrangements set out herein and instead extends to encompass all arrangements, and modifications and alterations thereto, which fall within the scope of the appended claims. For example, it will be apparent to persons skilled in the art that adaptive optical techniques of the type previously described may readily be applied to the SIO technique described herein, with similar benefits (the application of such techniques being straightforward for persons of ordinary skill in the art).

It will further be appreciated by persons skilled in the art that in the aforementioned embodiment where an object is simultaneously illuminated by three discrete beams of light from separate light sources, an equivalent arrangement would be to provide a single light source that is subsequently split (for example by a plurality of suitable filters) into the aforementioned three discrete beams of light. Such a modification should be considered as being within the scope of the present invention. An advantage of such an arrangement, as compared to a system that employs discrete RGB light sources, is that the wavelengths of light used to illuminate the object can more easily be varied—for example by using different sets of filters.

In addition, whilst in the arrangement depicted in FIG. 5 it is preferred for the reference light source 42 to generate incoherent light, it is anticipated that one could instead arrange for the light source to generate coherent light. However, in such circumstances a coherent light source would tend to generate artefacts in the images, and it would likely be difficult (i.e. computationally intensive) to distinguish these artefacts from landmarks in those images. In this light of this, it is preferred (but not essential) for the light source 42 to output incoherent light.

It should also be noted that whilst the accompanying claims set out particular combinations of features described herein, the scope of the present invention is not limited to the particular combinations hereafter claimed, but instead extends to encompass any combination of features herein disclosed.

The invention claimed is:

1. An optical imaging system for in-vivo retinal imaging, the system comprising:
   a first source for generating a reference beam of light at a first wavelength,
   a second source for generating incoherent light at a second wavelength different to said first;
   an optical imaging sub-system configured to split light from said second source into a plurality of beams, to introduce a path difference between said beams of light, and recombine those beams to form an interference fringe pattern that is imaged on a subject;

a video camera configured to capture successive images of the subject as the subject is illuminated with light from said optical imaging subsystem;

a reference image capture device configured to capture successive images of the subject as the subject is illuminated with light from said first source, said reference image capture device and said video camera being synchronized to successively capture images at substantially the same points in time; and a processor operable to process successive images captured by said reference image capture device to determine an extent to which the subject has moved between successive images, said processor being configured to derive, from the determined extent of movement, an indication of a phase shift in the interference fringe pattern, captured by the video camera, that is attributable to said determined movement.

2. A system according to claim 1, wherein said processor is configured to select from the successive images captured by said video camera, at least three images that are associated with relative phase shifts that are appropriate for combination of those images to provide a three-dimensional image of the subject.

3. A system according to claim 2, wherein said processor is configured to select images with a relative phase difference of $\phi 0$, $\phi 0+2\pi/3$ and $\phi 0-2\pi/3$, or more than three images with other combinations of relative phase differences.

4. A system according to claim 3, wherein said video camera is configured to be sensitive to a range of wavelengths of light that includes said second wavelength.

5. A system according to claim 4, wherein said second source can be swept over said range of wavelengths.

6. A system according to claim 5, wherein said processor is operable to combine images to generate a multispectral three-dimensional image of the subject.

7. A system according to claim 1, wherein said reference image capture device comprises a video camera.

8. A system according to claim 7, wherein said reference image capture device video camera is tuned for detecting light of said first wavelength.

9. A system according to claim 1, wherein said video camera is tuned to detect light of said second wavelength.

10. A system according to claim 1, wherein said optical imaging subsystem comprises a Michelson interferometer having a first branch, a second branch and a beamsplitter for directing incident light to each of said branches.

* * * * *